(12) United States Patent
Tsumura et al.

(10) Patent No.: US 6,975,386 B2
(45) Date of Patent: Dec. 13, 2005

(54) FILM QUALITY INSPECTING METHOD AND FILM QUALITY INSPECTING APPARATUS

(75) Inventors: Akira Tsumura, Yokohama (JP); Wataru Yamada, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 236 days.

(21) Appl. No.: 10/158,001

(22) Filed: May 31, 2002

(65) Prior Publication Data

US 2003/0016349 A1    Jan. 23, 2003

(30) Foreign Application Priority Data

Jun. 1, 2001  (JP) ............................ 2001-166409
Jul. 31, 2001  (JP) ............................ 2001-231762

(51) Int. Cl.[7] .......................................... G01N 21/55
(52) U.S. Cl. ........................................ 356/30; 356/445
(58) Field of Search .................. 356/30–31, 445–448, 356/237.1, 237.2; 438/16

(56) References Cited

U.S. PATENT DOCUMENTS

| 5,898,181 A | 4/1999 | Vurens |
| 5,982,482 A | 11/1999 | Nelson et al. |
| 6,195,163 B1 * | 2/2001 | Thakur et al. ............... 356/448 |
| 6,218,198 B1 * | 4/2001 | Imao et al. ................... 438/16 |

FOREIGN PATENT DOCUMENTS

| EP | 0660076 A2 | 6/1995 |
| JP | 3-97219 | 4/1991 |
| JP | 6-224276 | 8/1994 |
| JP | 6-244255 | 9/1994 |
| JP | 8-51078 | 2/1996 |
| JP | 10294346 A | 11/1998 |
| JP | 11-121378 | 4/1999 |
| JP | 11-274093 | 10/1999 |
| JP | 2000021943 A | 1/2000 |
| JP | 2000-133614 | 5/2000 |
| JP | 2000292128 A | 10/2000 |
| JP | 2001-110864 | 4/2001 |

* cited by examiner

*Primary Examiner*—Richard A. Rosenberger
(74) *Attorney, Agent, or Firm*—Finnegan, Henderson, Farabow, Garrett & Dunner, L.L.P.

(57) ABSTRACT

A film quality inspecting method comprising applying a measuring beam having a specific wavelength to an annealed silicon film formed on a substrate in a direction inclined with respect to the silicon film, measuring a reflection intensity or reflectivity of a reflection beam reflected by the silicon film as a result of the application, and inspecting a film quality of the silicon film based on a measurement value obtained by the measurement.

17 Claims, 5 Drawing Sheets

FILM QUALITY INSPECTING METHOD AND FILM QUALITY INSPECTING APPARATUS

CROSS-REFERENCE TO RELATED APPLICATIONS

This application is based upon and claims the benefit of priority from the prior Japanese Patent Applications No. 2001-166409, filed Jun. 1, 2001; and No. 2001-231762, filed Jul. 31, 2001, the entire contents of both of which are incorporated herein by reference.

BACKGROUND OF THE INVENTION

1. Field of the Invention

The present invention relates to a method and apparatus for inspecting a film quality of a polysilicon film formed on a substrate of, for example, an LCD (Liquid Crystal Display).

2. Description of the Related Art

In the manufacturing of an LCD, a laser beam is often applied to an amorphous silicon film (hereinafter referred to as a-Si) film formed on a substrate of the LCD to thereby transform it into a poly-silicon (hereinafter referred to as p-Si) film, thus forming a semiconductor film having a high electron mobility. In this case, an excimer laser beam is applied to the a-Si film by the use of an ELA (Excimer Laser Anneal) method.

According to a process using this ELA method, the a-Si film is melted and crystallized instantaneously to give less thermal damages to the substrate, thus making it possible to form a p-Si film by a low temperature process at about 450° C. or less. This gives an advantage of being able to form the p-Si film using an inexpensive glass substrate with a large area.

The electron mobility is here indicated as $\mu=|vd/E|(cm^2/SV)$, which gives a value/unit field of an average moving speed (drift speed: vd (cm/s)) of the electrons in crystal when an electric field E (V/cm) is applied to the crystal.

By using such a p-Si film, a TFT (Thin Film Transistor) with a high electron mobility can be formed on a glass substrate by a low temperature process. By using a p-Si film and a TFT, the problem can be solved to thereby obtain a thin and high-definition LCD of a so-called driver monolithic type in which a driver-section TFT and a picture-element section TFT are formed on a glass substrate.

When an a-Si film is transformed into a p-Si film through annealing by use of the laser beam, however, it is necessary to monitor whether it is formed into an appropriate crystal state (particulate diameter: 0.2–1.0 μm or more).

In monitoring of the crystal state, to check the crystal state the securest technology is to monitor the entire glass substrate directly through an optical microscope, which method however cannot possibly be applied to a field production line. To automate this method so that it may match the actual production line, there is available a technology disclosed in Jpn. Pat. Appln. KOKAI Publication No. 8-51078, which utilizes correlation between a crystallization ratio and a refractive index of a film to determine the refractive index using a semiconductor laser ellipsoid with a wavelength of 1294 nm, thus deciding whether a relevant product is to be accepted or rejected.

Furthermore, for example, Jpn. Pat. Appln. KOKAI Publication No. 3-97219 discloses a technology for, while applying an inspecting beam, optimizing the crystal state of the substrate to be processed, on the basis of a resultantly detected beam intensity.

Furthermore, Jpn. Pat. Appln. KOKAI Publication No. 6-244276 discloses a technology for, when detecting/evaluating a change in phase such as a crystal or amorphous state of a semiconductor film by applying energy beam, applying an annealing laser beam vertically to the semiconductor film to receive a resultant reflection beam spectrally so that a spectral reflectivity distribution thereof may be compared to data stored in a database, thus evaluating the crystallization state of the semiconductor film.

Furthermore, Jpn. Pat. Appln. KOKAI Publication No. 6-244255 discloses a technology for using a spectral profile of the reflection beam of a silicon film to thereby calculate its poly-crystallinity ratio and amorphous-ness ratio.

Furthermore, Jpn. Pat. Appln. KOKAI Publication No. 11-274093 discloses a technology for applying a processing laser beam and a measuring laser beam simultaneously to a silicon film to monitor their reflectivity, thus determining the layer state of the silicon film.

Furthermore, Jpn. Pat. Appln. KOKAI Publication No. 2000-133614 discloses a technology for applying the laser beam in pulse to a silicon layer to determine a state of the silicon layer based on a time-wise attenuating waveform.

Furthermore, Jpn. Pat. Appln. KOKAI Publication No. 11-121378 discloses a technology for measuring a reflectivity of a glass substrate on its back side on which a silicon layer is formed, to determine a state of the silicon layer based on the measurement of the reflectivity.

By the technology disclosed in Jpn. Pat. Appln. KOKAI Publication No. 8-51067 for optimizing the crystal state of the substrate to be processed only based on the intensity of the inspecting beam, however, the substrate cannot be heated sufficiently, so that a part thereof where the a-Si film is not melted can be known for sure but a part thereof where the a-Si film is melted but fine crystal particulate (particulate diameter: 0.01–0.02 μm approximately) transformed into a granular state owing to excessive heating, that is, a part where micro-crystal silicon (μ-cSi) is formed cannot be detected.

This part where the granular-state fine crystal particulate is formed has an extremely low average electron mobility, not higher than a value of 100 $(cm^2/S \cdot V)$ supposed to be appropriate in formation of a driver section TFT. By this method, therefore, it is impossible to know whether a p-Si film is formed uniformly, thus possibly deteriorating the yield of manufacturing the TFT.

Furthermore, by the technology disclosed in Jpn. Pat. Appln. KOKAI Publication No. 3-97219 for applying a visible reference laser beam to a site where the excimer laser beam is being applied to evaluate a crystallization level of the site based on a change in intensity of the resultant transmission or reflection beam, there is a problem that it is impossible to obtain information of re-crystallization after actual poly-crystallization.

Furthermore, by this method, the excimer laser beam is applied in pulse by a few shots, so that when the visible reference laser beam is applied, its transmission or reflection beam changes in intensity, thus giving rise to a problem of difficulty to decide crystallinity. Besides, there is a problem of complexity of an apparatus for electrically processing and detecting the time-wise changing intensity of the transmission or reflection beam.

Furthermore, by the technology disclosed in Jpn. Pat. Appln. KOKAI Publication No. 8-51078 for measurement by use of a semiconductor laser ellipsoid, it is necessary to know an accurate film thickness beforehand for calculating the refractive index. Besides, calculation thereof takes much time, thus deteriorating the throughput. Moreover, an optical system for the measurement apparatus becomes large and complicated.

Furthermore, by the technology disclosed in Jpn. Pat. Appln. KOKAI Publication No. 6-224276, the annealing laser beam is applied vertically to a semiconductor film to receive its reflection beam spectrally in order to then compare its spectral reflectivity distribution to the data stored in a database and evaluate a crystallization state of the semiconductor film, so that it is necessary to measure the spectral reflectivity of the semiconductor film for each waveform and also create the data of its consecutive profiles, thus suffering from complex data processing. This problem holds true also with the technology disclosed in Jpn. Pat. Appln. KOKAI Publication No. 6-244255.

Furthermore, by the technology disclosed in Jpn. Pat. Appln. KOKAI Publication No. 11-274093, the processing laser beam and the measuring laser beam are applied simultaneously to a silicon film to monitor the reflectivity thereof in order to detect a layer state of the silicon film, so that the reflectivity of the processing laser beam and that of the measuring laser beam are added to each other to give rise to mutual interference of the beam, thus disqualifying the method for use in accurate measurement.

Furthermore, by the technology disclosed in Jpn. Pat. Appln. KOKAI Publication No. 2000-133614, the laser beam is applied in pulse to a silicon layer to determine a state of the silicon layer based on the shape of the time-wise attenuating waveform, thus complicating the processing of data such as waveform data.

Furthermore, by the technology disclosed in Jpn. Pat. Appln. KOKAI Publication No. 11-121378, reflectivity of a glass substrate is measured on its back side on which a silicon layer is formed, to determine a state of the silicon based on the measurement, thus making it impossible to directly determine the surface state of the silicon layer itself.

In view of the above, it is an object of the present invention to provide a film quality inspecting method and apparatus which can inspect a crystal state of a silicon substrate speedily and simply.

BRIEF SUMMARY OF THE INVENTION

A film quality inspecting method according to claim 1 comprises: applying a measuring beam having a specific wavelength to an annealed silicon film formed on a substrate in a direction inclined with respect to the silicon film; measuring a reflection intensity or reflectivity of a reflection beam reflected by the silicon film as a result of the application; and inspecting a film quality of the silicon film based on a measurement value obtained by the measurement.

A film quality inspecting method according to claim 11 comprises: applying a beam to an annealed silicon film formed on a substrate; detecting a reflection beam having a first range wavelength reflected by the silicon film as a result of the application to obtain a first detection signal; detecting a reflection beam having a second range wavelength reflected by the silicon film as a result of the application to obtain a second detection signal; and inspecting a film quality of the silicon film based on the first and second inspection signals corresponding to about the same region on the silicon film.

A film quality inspecting apparatus according to claim 16 comprises: a stage on which a substrate having an annealed silicon film thereon is mounted; a beam source which emits a measuring beam to be applied to the silicon film on the substrate mounted on the stage; application devices which selectively apply beams having wavelengths in different ranges of the beams emitted from the beam source to the silicon film; an optical sensor which receives the reflection beam reflected by the silicon film when applied by the application devices to convert the reflection beam into an electric signal; and a film quality inspection device which inspects the film quality of the silicon film based on the electric signal output from the optical sensor.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

The following will describe in detail the preferred embodiments of the present invention with reference to the drawings.

Since amorphous silicon (hereinafter referred to as a-Si) can be manufactured by a low temperature process even at a temperature of 350° C. or less, it is possible to use an inexpensive glass substrate and also to make a large screen of it. To compensate for a low electron mobility thereof, however, a TFT size must be large, thus giving rise to a problem of a decrease in numerical aperture in high definition applications. Further, it cannot incorporate an driver IC therein generally.

To solve these problems of the a-Si, poly-silicon (hereinafter referred to as p-Si) is attracting the attention of the industries. As a p-SiTFT, first a high-temperature p-SiTFT was developed following a mono-crystal silicon MOS-FET. The high-temperature p-Si has an electron mobility about 100 times as much as that of a-Si. Accordingly, the TFT can be compacted without departing from a tolerance of processing accuracy and also have a higher numerical aperture. Besides, it can incorporate a driver IC therein.

The high-temperature p-Si requires a high temperature process at 900° C. or more for its production, so that an expensive quartz glass must be used for its manufacture. Furthermore, the quartz glass can be given up to a diameter of 8 inches and so cannot be implemented as a large-screen LCD (Liquid Crystal Display), thus being limited to a small size application such as a projection one.

In view of the above situation, there has been a desire for the developments of p-Si that has almost the same electron mobility as high-temperature p-Si, that a glass substrate made thereof can also be used as a-Si, and also that a large screen can be made thereof. That is low-temperature p-Si.

The low-temperature p-Si can be manufactured by the low-temperature process by utilizing an excimer laser annealing method. Accordingly, a glass substrate made of p-Si almost as large as that made of a-Si can be used to manufacture a TFT-LCD.

The TFT made of p-Si can be compacted and also incorporate a driver IC and so can solve such problems inherent to the TFT-LCD made of a-Si as deterioration in numerical aperture, restrictions on higher definition, etc., thus giving such features preferable for a mobile LCD as higher brightness, lower power dissipation, higher definition, improved durability, lighter weight, smaller thickness, etc.

Besides, the higher the laser power applied on a-Si in its laser annealing, the larger crystal is formed to increase the electric conductivity, thus improving device characteristics. If the laser power is too high so that the crystal may become granular, however, the electric conductivity decreases conversely, thus making the device defective as well known generally.

The present inventor worked out a basic concept of inspecting and managing such a crystal state by observing, using a spectral ellipsoid, a relationship between the crystal state and the reflectivity along a process for poly-crystallizing a-Si by laser annealing and analyzing a result of the observation.

Figure 1:
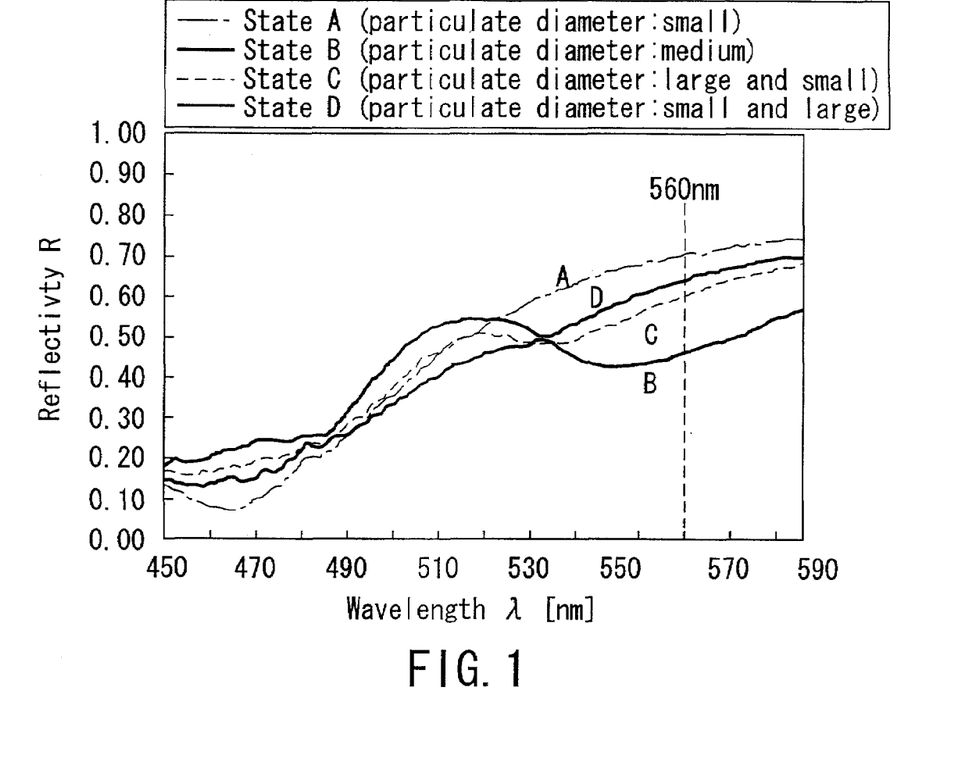
FIG. 1 is a graph for showing a result of observing, by using a spectral ellipsoid, a relationship between a crystal state and reflectivity of a p-Si film according to a first embodiment of the present invention.

FIG. 1 is a graph for showing a result of observing the relationship between the crystal state and the reflectivity using a spectral ellipsoid. In the graph of FIG. 1, the horizontal axis indicates a wavelength and the vertical axis, the reflectivity for each of the crystal states. The crystal states are classified into states A, B, C, and D according to the crystal particulate diameter. The state A corresponds to a small particulate diameter, the state B corresponds to a medium particulate diameter, the state C corresponds to a mixture of a large particulate diameter in a major proportion and an extremely small particulate diameter in a minor proportion. The state D corresponds to a mixture of an extremely small particulate diameter in a major proportion and a large particulate diameter in a minor proportion. That is, the state B indicates an acceptable product, which must be used commercially. The state C indicates an upper limit above which the product is unacceptable and the states D and A indicate an unacceptable product.

If the crystallization progresses further, the state B shifts to the state C and then to the state D where the extremely small particulate diameter increases in proportion. If such extremely small particulate diameter occurs, the product is not appropriate and so is unacceptable. If the particulate is crystallized in a wavelength range of 550–570 nm, the reflectivity is observed to rise to 0.55 or more. In the wavelength range of 450–500 nm, on the other hand, the particulate exhibits crystallization as well as a decrease in reflectivity down to 0.5 or less.

The reflectivity observed at a wavelength of 560 nm exhibits 0.55 or less for the medium particulate diameter but 0.55 or more for the large particulate diameter, thus discriminating them from each other clearly.

That is, when a laser beam with a wavelength of 560 nm is applied not through an optical filter or an inspection beam is applied through it to the surface of a p-Si substrate and if the substrate exhibits a reflectivity of 55% or less, it is decided to be acceptable and, otherwise, unacceptable.

In an inspection step, the surface of a p-Si substrate is scanned with the laser beam having a wavelength of 560 nm not through an optical filter or with the inspection beam through it to check which positions of the surface of the p-Si substrate have a defect, thus counting all the defects. This result is fed back to the annealing conditions to decrease the laser power in the next laser annealing of the a-Si substrate, thus stabilizing the crystal state.

In this case, low reflectivity of the surface of the p-Si substrate indicates that the intensity of the reflection beam is also low. Therefore, by measuring the reflectivity or the intensity of the reflection beam, it is possible to inspect the crystal state of the silicon of the p-Si substrate in order to decide defective/non-defective states of the p-Si substrate, thus preventing a defective product from going to the subsequent steps.

The following will describe a thin film processing apparatus based on the above-mentioned principle according to the present invention.

Figure 2:
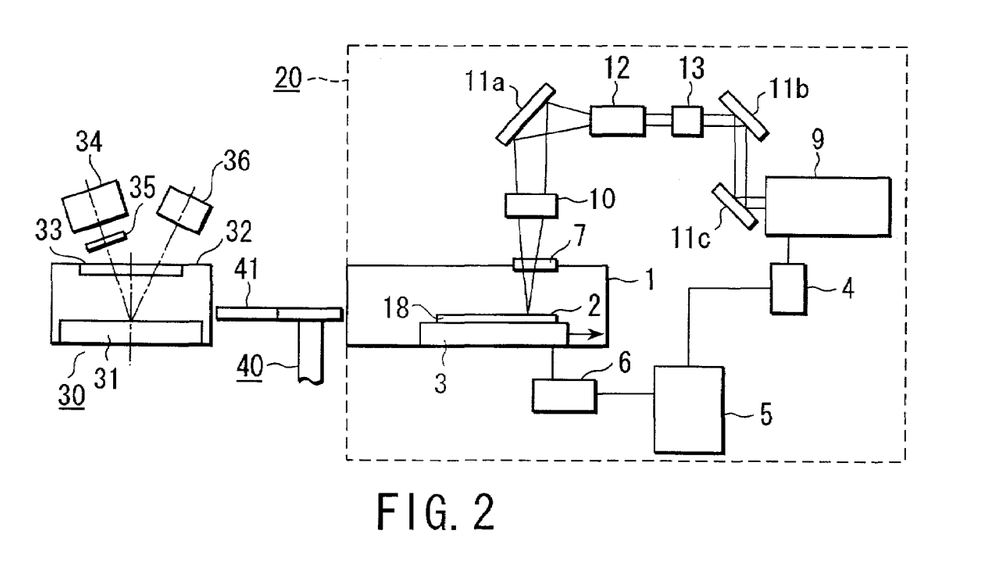
FIG. 2 is a configuration diagram for showing a laser annealing apparatus and a poly-crystal film inspecting apparatus according to the first embodiment of the present invention.

FIG. 2 is a configuration diagram for showing a thin film processing apparatus provided with a laser annealing apparatus 20 and a poly-crystal film inspecting apparatus 30.

In the thin film processing apparatus, the laser annealing apparatus 20 and the poly-crystal film inspecting apparatus 39 are arranged horizontally with a conveyor robot sandwiched therebetween. The conveyor robot 40 has such a construction that an arm 41 thereof can move into the laser annealing apparatus 20 and the poly-crystal film inspecting apparatus 20 to convey the p-Si substrate, that is, a processing subject 2 in the laser annealing apparatus 20 into the poly-crystal film inspecting apparatus 30.

The laser annealing apparatus 20 is provided with an enclosed reaction container 1. The reaction container 1 has therein an XY scanning table 3 for moving the processing subject 2 (a-Si substrate) as mounted thereon. This XT scanning table 3 is controlled in driving by a table driving system 6 via a system control system 5 controlled by a host computer 4.

In a ceiling of the reaction container 1 is formed a transparent excimer laser beam injection window 7. Above this excimer laser beam injection window 7 are disposed an image forming lens 10, a mirror 11a, a beam homogenizer 12, a variable attenuator 13, mirrors 11b and 11c, and an excimer laser beam oscillator 9 in this order.

Although this excimer laser beam oscillator 9 uses XeCl which oscillates a beam having a wavelength of 308 nm as its laser beam medium, any other media such as ArF or KrF may be used. The excimer laser beam oscillator 9 is controlled by the host computer 4.

In this configuration, in a state where a glass substrate (a-Si substrate) on which is formed an a-Si film, which is the processing subject, is mounted on the XY scanning table 3, an excimer laser beam is oscillated from the excimer laser beam oscillator 9. The excimer laser beam thus oscillated passes through the mirrors 11c and 11b and then enters the line beam homogenizer 12 to be shaped into a line (for example, a beam cross section of a stripe of 200 mm×0.5 mm) with a top flat energy level. Thus obtained line beam is applied by the image forming lens 10 through the mirror 11a onto the glass substrate on which is formed the a-Si film, which is the processing subject 2, to thereby scan the XY scanning table 3, thus crystallizing all the surface of the a-Si film formed on the glass substrate. In this case, laser beam output provided by the excimer laser oscillator 9 is controlled at a fluence suitable for poly-crystallization by the variable attenuator.

Note here that the reaction container 1 contains dried air having such a composition as to enable controlling a nitrogen or vacuum atmosphere.

The processing subject 2 (p-Si substrate) thus formed to provide a predetermined particulate diameter in such a laser annealing apparatus 20 is carried by the conveyor robot 40 to the poly-crystal film inspecting apparatus 30. Specifically, the arm 41 of the conveyor robot 40 moves into the reaction container 1 through its opening/closing type door provided on its side wall and grips the p-Si substrate mounted on the XY scanning table 3 in the reaction container 1 and then carries it onto the stage 31 provided in the poly-crystal film inspecting apparatus 30.

Figure 3:
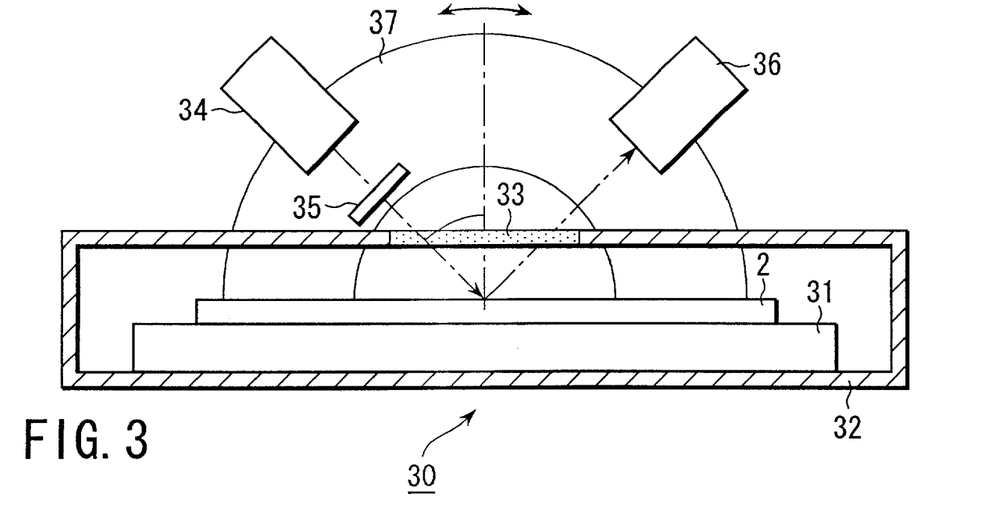
FIG. 3 is a schematic configuration diagram for showing the poly-crystal film inspecting apparatus.

As shown in FIG. 3, the poly-crystal film inspecting apparatus 30 comprises in a cabinet 43 the stage 31 on which the p-Si substrate, which is the processing subject 2, processed in the previous step is mounted and, above it, a beam projecting section 34 for projecting the measuring beam from a beam source (not shown) onto the p-Si substrate through a skylight 33 formed in the cabinet 32 and an optical filter 35 disposed in front of the beam projecting section 34 on its optical axis for extracting only such a beam as having a predetermined wavelength from the measuring beam emitted from the beam source. Besides, there are provided a beam receiving section 36 for receiving the beam reflected by the p-Si substrate and a goniometer 37 for adjusting an incident angle of the beam.

As the beam source is employed a semiconductor laser or a halogen lamp, to apply the beam to the p-Si substrate at an angle inclined by 10 degrees or so (up to 15 degrees) with respect to the perpendicular. If a semiconductor laser is employed as the beam source, the beam projecting section 34 has a built-in power detecting system (not shown) for monitoring the laser power.

The measuring beam applied via the optical filter 35, therefore, is reflected by the surface of the p-Si substrate and then made incident upon the beam receiving section 36 obliquely at an angle inclined by 10 degrees or so with respect to the perpendicular. The reflection intensity of the beam made incident upon the beam receiving section 36 is measured, based on which a reflectivity is calculated by reflectivity calculating means (not shown). Thus obtained reflection intensity and reflectivity can compared by identifying means (not shown) to data of a measurement of the intensity of the reflection beam of the p-Si substrate, thereby identifying a state of the film quality of an arbitrary p-Si substrate which has received the beam.

In a case where, for example, a laser beam with a wavelength of 560 nm or the optical filter 35 is used according to the conclusion mentioned above with reference to FIG. 1, if thus calculated reflectivity of the p-Si substrate is 55% or less, this substrate is decided to be acceptable and, otherwise, unacceptable.

Furthermore, the surface of the p-Si substrate is thoroughly scanned to check which positions of the surface have a defect to thereby calculate a total sum of the all defects. Based on the result, the annealing conditions are fed back so as to decrease the laser power in the next laser annealing of the a-Si substrate, thus stabilizing the crystal state of the a-Si substrate caused by laser annealing thereof.

The fluence of the laser power can be controlled by controlling a transmission factor of the variable attenuator. Alternatively, it can be controlled by controlling the output power of the laser oscillator 9 to thereby adjust the laser output.

It is to be noted that by providing a plurality of sets each consisting of the above-mentioned beam projecting section 34 and beam receiving section 36 so that these sets may perform processing on their respective regions simultaneously, thus increasing the overall processing speed.

As mentioned above, by the present embodiment, decision is made simply only on the basis of the intensity of the reflection beam from the p-Si substrate, so that the measurement time can be reduced greatly as compared to that by the ellipsoid method which analyzes the polarization condition, thus simplifying the measurement system itself.

Besides, by arranging a plurality of measurement optical systems, it is possible to expand a range that can be detected at a time, thus improving the throughput.

Furthermore, since the incident angle of the optical system can be adjusted by the goniometer 37, it is possible to select an incident angle at which the reflection beam intensity changes remarkably with a change I the crystal state. It was confirmed by experiments that stable detection is possible without affected by roughness in the surface when the incident angle and the reflection angle are inclined by 10 degrees or so (not more than 15 degrees) with respect to the perpendicular.

Although the present embodiment decides acceptableness/unacceptable-ness based on a threshold value of the reflectivity, the threshold value may change with the film thickness. On the surface of the p-Si substrate, however, the defective positions are scattered in many cases and therefore the most of the regions is non-defective, so that the surface of the p-Si substrate may be scanned thoroughly to then obtain a histogram of the reflectivity in order to decide a region which does not fall in a population of the acceptable ones to be non-acceptable. By this method, it is possible to accurately identify a defective position even with the threshold value fluctuating with each of the p-Si substrates.

It is thus possible to stable the crystal state given by the laser annealing processing, thus improving the yield.

FIGS. 4–10 show the second embodiment of the present invention.

As mentioned above with the first embodiment, by the low-temperature p-Si can be manufactured by a low temperature process by utilizing excimer laser annealing processing. It is thus possible to commercially produce a TFT-LCD made of p-Si using a large glass substrate having almost the same size as that by a-Si.

By using p-Si, the TFT can be small sized and a driver IC can be incorporated, to solve the problems such as deterioration in numerical aperture, restrictions on higher definition, etc., thus giving such features suitable for a mobile LCD as higher brightness, lower power dissipation, higher definition, improved durability, lighter weight, smaller thickness, etc.

Figure 4:
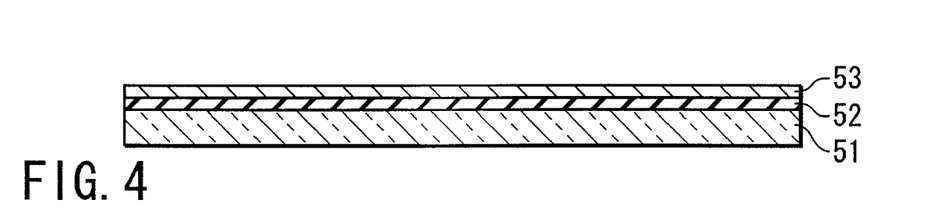
FIG. 4 is a cross-sectional view for showing a state where an a-Si film is formed on a glass substrate according to a second embodiment of the present invention.
Figure 5:
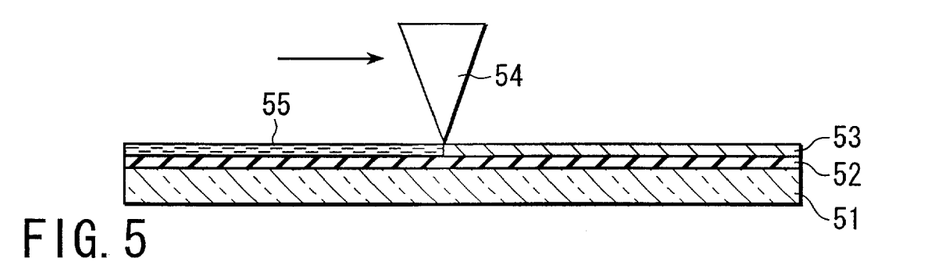
FIG. 5 is a cross-sectional view for showing a state where laser annealing processing is conducted on the a-Si film on the glass substrate.
Figure 6:
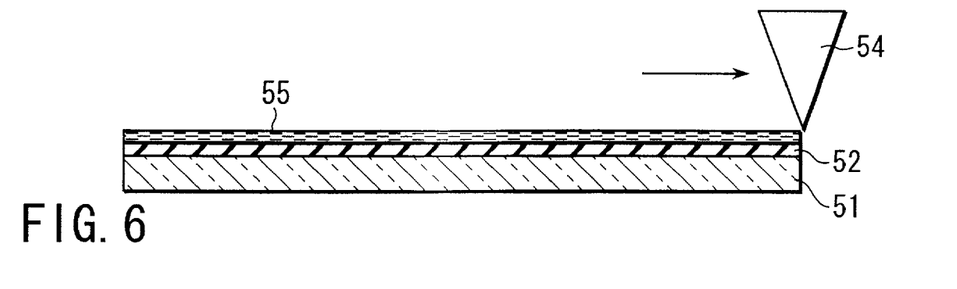
FIG. 6 is a cross-sectional view for showing a state where a p-Si film is formed throughout the glass substrate.

As is clear from the schematic diagrams shown in FIGS. 4–6, to manufacture on a TFT in which a p-Si film is formed on a glass substrate 51, it is necessary to form the p-Si film on the glass substrate 51 without deforming the glass substrate 51. To form the p-Si film under such restrictions, as shown in FIG. 4, first an underlying protection film 52 made of silicon oxide etc. is formed by plasma-enhanced CVD (PECVD) on the surface of the substrate 51 made of clean non-alkali glass etc.

Next, an a-Si film 53 is formed by PECVD on the surface of the underlying protection film 52.

Next, as shown in FIG. 5, laser beam with a higher energy density obtained by concentrating laser beam 54 is applied onto the a-Si film 53 to carry out laser annealing processing thereon to thereby anneal and poly-crystallize the a-Si film 53, thus forming a p-Si film 55.

Next, as shown in FIG. 6, by applying a laser spot, the a-Si film 53 formed throughout the surface of the substrate 51 is poly-crystallized.

Note here that in laser annealing of the a-Si film 53, the higher the power of the laser beam employed, the larger crystal is formed to improve the electron mobility, thus improving the electrical device characteristics also. If the laser beam power becomes too high in excess of a certain value, the particulate diameter of the crystal decreases suddenly. If the crystal particulate becomes small, the electron mobility decreases conversely, thus deteriorating the device performance as well known generally.

Furthermore, it is not always preferable that the crystal particulate diameter be larger, instead it is necessary to provide electron mobility that matches an electrical circuit formed on the surface of the substrate 51, that is, to poly-crystallize the particulate so that it may have an appropriate particulate diameter. For this purpose, it is necessary to inspect and manage the diameter of the particulate formed on the surface of the substrate 51.

The present inventor worked out a basic concept of inspecting and managing such a crystal state by applying beams with different specific wavelengths to the crystal of the a-Si film 53 as poly-crystallized by laser annealing, to detect the intensity of the reflection beam for each of these wavelengths of the applied beams and then combine the results, thus deciding the crystal state highly accurately.

Figure 7:
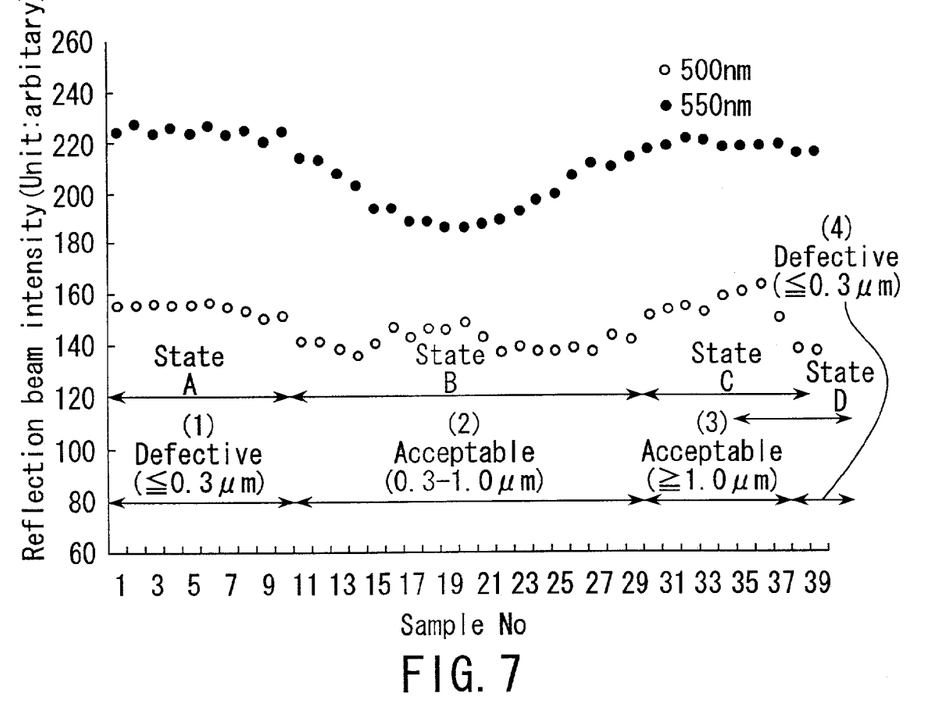
FIG. 7 is an illustration for showing data of a distribution of reflection beam.

FIG. 7 show distributions of the data of measurements of the intensity (average intensity) of the reflection beams with specific wavelengths (500 nm, 550 nm) applied to samples prepared in correspondence to the degree of growing of the particulate diameter of the a-Si film 53 as processed by laser annealing. In FIG. 7, the vertical axis indicates the reflection beam intensity and the horizontal axis indicates a sample number corresponding to the degree of progressing of crystallization (change in particulate diameter), based on which the distribution is grouped into four regions (1–4).

In this case, based on the growing degree of the crystal, region 1 corresponds to a particulate diameter of 0.3 $\mu$m or less, region 2 corresponds to a particulate diameter of 0.3–1.0 $\mu$m or more, region 3 corresponds to a particulate diameter of 1.0 $\mu$m or more, and region 1 corresponds to a particulate diameter of 0.3 $\mu$m or less.

In FIG. 7, the application beam takes on a wavelength of 550 nm (540–560 nm) with a green filter employed and a wavelength of 500 nm (490–510 nm) with a blue filter employed.

As is clear from the distribution in each of the regions in FIG. 7, region 2 is lower in reflection beam intensity than regions 1, 3, and 4 and so can be discriminated from these. Region 3 indicating acceptable-ness, however, has almost the same distribution range of the reflection beam intensity as that of regions 1 and 4 and so cannot be discriminated from these. Besides, generally, regions 1 and 3 scarcely coexist on the same substrate, so that it is enough if regions 1 and 2 or regions 2, 3, and 4 and can be discriminated from each other. If, therefore, regions 3 and 4 can be discriminated from each other, all of the four regions can be from each other.

Next, in terms of distribution in each region at a wavelength of 500 nm, the reflection beam intensity is distributed largely different between regions 3 and 4, which can therefore be discriminated from each other easily. Accordingly, by combining inspection results at wavelength of 550 nm and 500 nm, it is possible to identify the crystal states accurately as sub-divided into the four regions.

The following will describe a method for manufacturing an LCD, which is a thin film processing apparatus of the present invention based on the above-mentioned principles.

Figure 8:
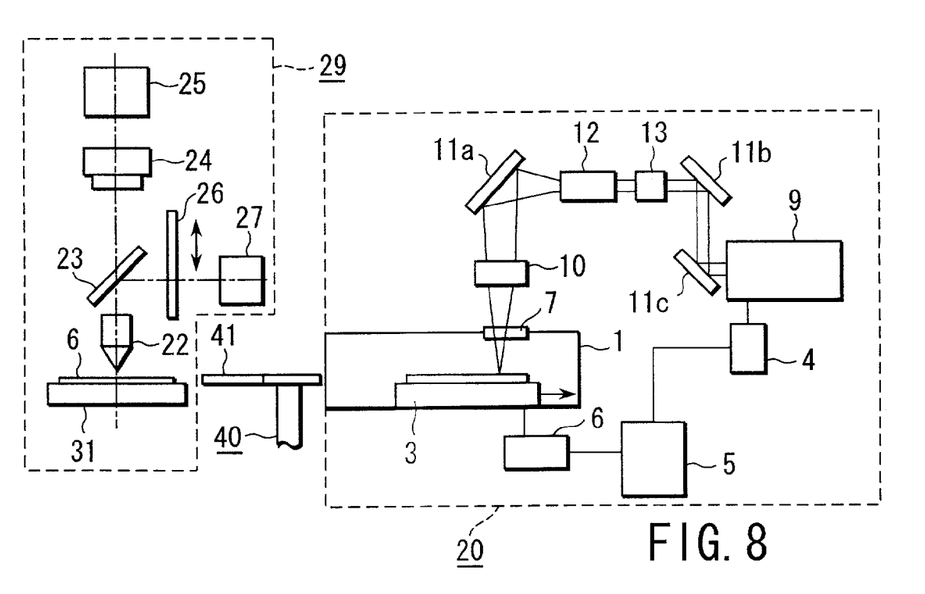
FIG. 8 is a configuration diagram for showing the laser annealing apparatus and the poly-crystal film inspecting apparatus.

FIG. 8 is a schematic configuration diagram for showing an LCD manufacturing apparatus provided with a laser annealing apparatus and a poly-crystal film inspecting apparatus 29 according to the second embodiment.

Note here that the laser annealing apparatus has the same components as those described with the above-mentioned first embodiment, so that they are indicated by the same reference numerals and their explanation is omitted here.

The processing subject (p-Si substrate 6) processed and formed by the laser annealing apparatus 10 so as to have a predetermined particulate diameter is carried by the conveyor robot 40 to a poly-crystal film inspecting apparatus 29. Specifically, the arm 41 of the conveyor robot 40 moves into the reaction container 1 through its opening/closing type door (not shown) provided on its side wall and grips the p-Si substrate 6 mounted on the XY scanning table 3 in the reaction container 1 and then carries it onto the stage 31 provided in the poly-crystal film inspecting apparatus 29.

Figure 9:
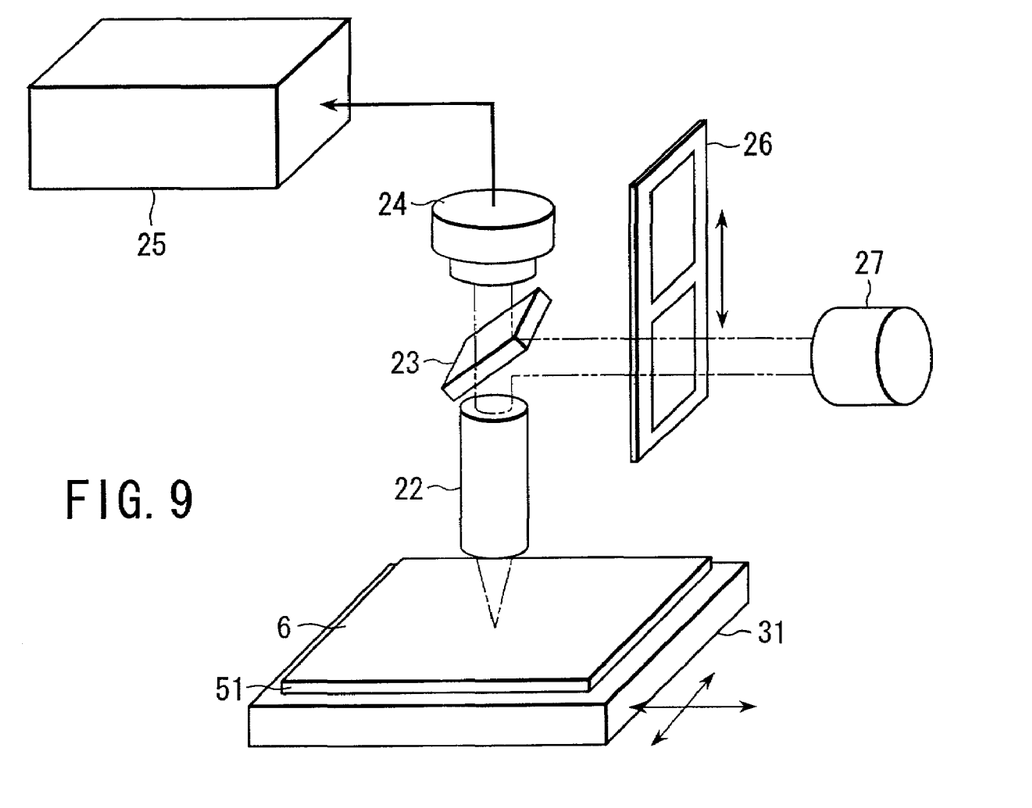
FIG. 9 is a perspective view for showing the poly-crystal film inspecting apparatus.
Figure 10:
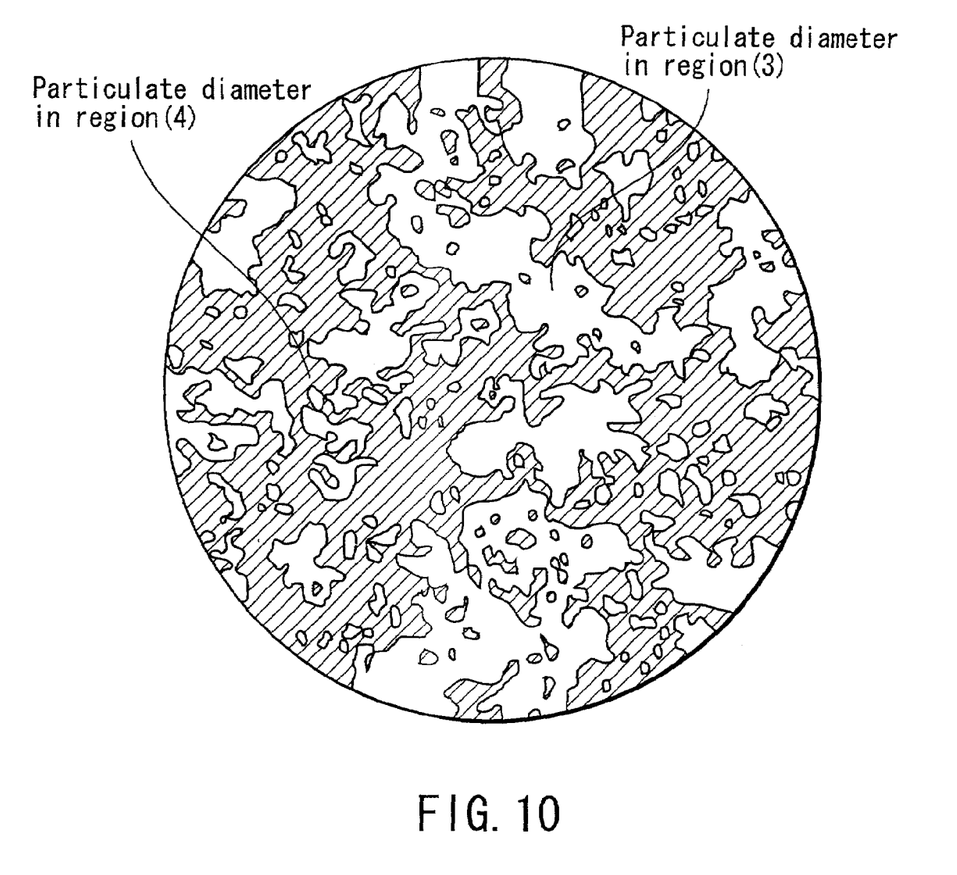
FIG. 10 is an illustration for showing an expanded screen of reflection beam sent from the p-Si film.

In the poly-crystal film inspecting apparatus 29, a detection optical system is disposed above the XY table 31, on which is mounted the glass substrate 51 with the p-Si substrate 55, which is the processing subject, formed thereon as shown in FIG. 10 also. This detection optical system has such a configuration that as viewed from the side of the XY table 31 are sequentially disposed along the optical axis a magnification optical system 22 and a half mirror 23 and also, on the transmission side along the optical axis of the half mirror 23 is disposed a two-dimensional beam sensor 24, which photo-electrically transfers an electric signal and then outputs it to an image processing/crystallinity deciding section 25. Besides, on the opposite side along the optical axis of the half mirror are provided a switch-over type wavelength selecting mechanism 26 and a multi-color beam source 27.

In this configuration, only a beam having a specific wavelength of the beams emitted from the multi-color beam source 37 such as a halogen lamp etc. is selected by the wavelength selecting mechanism 26 and passes via the half mirror 33 through the magnification optical system 32 to thereby be applied onto the surface of the p-Si film 55. The beam reflected by the surface of the p-Si film 55 is magnified by the magnification optical system 22 with an arbitrary magnification to then be projected onto the surface of the two-dimensional beam sensor 24 in an image. Thus projected image of the film is transferred into an electric signal by the two-dimensional beam sensor 24 and then output to the mage processing/crystallinity deciding section 25.

Note here that the p-Si film 55 is irradiated throughout its surface with a beam having a first specific wavelength gradually as the XY table 31 moves, so that correspondingly the resultant reflection beam is projected to the surface of the two-dimensional beam sensor 24, a result of which is input as an electric signal to the image processing/crystallinity deciding section 25.

Next, the wavelength selecting mechanism 36 is switched to select only a beam having a second specific wavelength. Subsequently, the same operations as those with the first specific wavelength are repeated to project the reflection beam from the surface of the p-Si film 55 onto the surface of the two-dimensional beam sensor 24, the result of which is then input to the image processing/crystallinity deciding section 25.

The image processing/crystallinity deciding section 25 processes the data obtained by transferring into the electric signal the reflection beams of the beams having the first and second specific wavelengths and combines the results of the processing, thus deciding by operations the state of the crystal based on the beam intensity of the image.

It is to be noted that that the crystal state must be inspected as magnified because the crystal is very small. Therefore, as shown in FIG. 10 illustrating the image, the surface of the p-Si film 55 is inspected as magnified by the magnification optical system 22.

It is to be noted that that FIG. 10 shows one example of the image obtained when a green beam is applied. In FIG. 10, a bright area indicates region 3 when the wavelength is 500 nm and a dark area indicates region (a in FIG. 7. Such an image as shown in FIG. 10 is taken in by the image processing/crystallinity deciding section 25 for deciding the crystal state for each of the areas based on the intensity of the image in these areas.

The following will describe the measurement results obtained by the poly-crystal film inspecting apparatus 29.

As mentioned above, the reflection beam intensity obtained when a beam with a specific wavelength is applied to the p-Si film 55 changes with the magnitude of the particulate diameter of the p-Si film 55. When green and blue beams are applied, in particular, as experimentally confirmed, the characteristics change remarkably owing to a change in the particulate diameter.

550 nm in FIG. 7 is a graph for showing a relationship between the particulate diameter and the reflection beam intensity when the green beam (with a wavelength of 540–560 nm) is applied, as mentioned above. 500 nm in FIG. 7, on the other hand, is a graph for showing the similar relationship when a blue beam (with a wavelength of 490–510 nm).

In FIG. 7, the horizontal axis indicates the sample numbers, which are discriminated from each other by a particulate diameter. In FIG. 17, sample numbers 38–39 indicate a region where the particulate diameter is very small, that is, as mentioned above, the laser beam energy density is too high and so the particulate diameter is reduced.

As shown in FIG. 7, when the green beam is applied, the beam is reflected most strongly to thereby provide a highest level of the intensity of the reflection beam in region 1 where the particulate diameter is 0.3 μm or less, region 3 where the particulate diameter is large as much as 1 μm or more, and region 4 where the particulate diameter is suddenly reduced, whereas in region 2 in which the particulate diameter is 0.3–1.0 μm, the reflection beam intensity decreases. Besides, generally there is a possibility of coexistence between regions 1 and 2 and also a similar possibility among regions 2, 3, and 4, whereas among regions 1, 3, and 4 there is a small possibility of this kind. By utilizing this, it is possible to discriminate in particulate diameter between regions 1 and 2 or between regions 2 and regions 3 and 4.

Furthermore, as for regions 3 and 4, when the blue beam is applied, as shown in FIG. 7, the reflection beam intensity is higher in region 3 and lower in region 4. Therefore, regions 3 and 4 can be discriminated from each other.

By utilizing a combination of the relationships between the reflection beam intensity and the particulate diameter when these green and blue beams with specific wavelengths are applied, regions 1, 2, 3 and 4 can be separated from each other. This makes it possible to inspect the state of the particulate diameter of the p-Si film 55.

The inspection results can be used to adjust the output of a laser oscillator 10 of a laser annealing apparatus 20, thus performing good and uniform laser annealing processing.

Although the above-mentioned embodiments have used the specific wavelength of 540–560 nm (first specific wavelength) and 490–510 nm (second specific wavelength), any other arbitrary combinations of the specific wavelengths may be employed as far as they may support each other in discrimination of the data. For example, they may be expanded to 480–570 nm as the first specific wavelength and 530–570 nm as the second specific wavelength.

Further, although the above-mentioned poly-crystal film inspecting apparatus 29 detects the intensity of the beam reflected by the p-Si film 55, it may detect the reflectivity from each of the regions to then process the resultant data.

Furthermore, in the apparatus for manufacturing the LCDs, the particulate state need not be inspected everywhere on the p-Si film in the poly-crystal film inspecting apparatus 29 but only needs to be inspected at an arbitrary sampling interval.

It is thus possible to stabilize the crystal state in laser annealing processing, thus improving the yield in manufacture.

Although the second embodiment has been described with reference to a film quality inspecting method using wavelengths only in two ranges, the present invention is not limited thereto; for example, three ranges or more of the wavelengths may be employed. Therefore, the film quality may be inspected using wavelengths in three or four ranges.

Furthermore, since it is clear that the reflectivity of the beam with a specific wavelength changes with a change in crystal state of the silicon film, the crystal state can be decided on the basis of the reflection beam. For example, according to the embodiments of the present invention, by applying a green beam, it is possible to discriminate between a crystal state with a particulate diameter of 0.3 μm or less and that with 0.3–1.0 μm, so that they can be discriminated from each other by using a green beam having a single wavelength. When a laser beam is applied under such conditions that the particulate diameter does not reach 1 μm clearly (region 3 in FIG. 7), such a method is useful as to inspect the film quality using only a beam having a single wavelength.

Alternatively, a method may be used for moving the substrate 51 as applying a beam with a first specific wavelength to acquire data of the resultant reflection beam intensity and then moving it as applying a beam with a second specific wavelength to acquire data of the reflection beam intensity throughout the surface of the substrate 51, so that based on these two data items the film quality is inspected throughout the surface of the substrate 51.

According to this method, the surface of the substrate 51 is thoroughly scanned by the laser beam with the first specific wavelength to acquire the data of the reflection beam intensity of a plurality of positions in a predetermined region and then by the laser beam with the second specific wavelength to acquire the data of the reflection beam intensity of the same plurality of positions in the predetermined region, so that based on each piece of the reflection beam intensity data obtained for each of the same positions, the film quality of the silicon film is inspected of each position. It is thus possible to decrease the number of times of switch-over by the wavelength selecting mechanism 26, thus reducing the inspection time.

Furthermore, although this second embodiment separates the application beams into two wavelength regions by using the wavelength selecting mechanism 26, it may be modified so that the wavelength can be received selectively. For example, the wavelength selecting mechanism 26 may be disposed on the upstream side of the beam sensor 34 or a dichroic prism may be used to space-wise separate the reflection beams into green and blue ones so that they can be imaged by two beam sensors respectively. By this method, each time they are applied, the intensity can be detected in two wavelength areas simultaneously, thus reducing the inspection time.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. A film quality inspecting method comprising:
   applying a light beam having a specific wavelength only within a range of 550 to 570 nm to an annealed silicon film formed on a substrate approximately perpendicularly to said silicon film;
   receiving a reflected beam and measuring a reflection intensity or reflectivity of the reflected beam;
   measuring a particle diameter of crystalline silicon of the silicon film based on the measured reflection intensity or reflectivity; and
   inspecting a film quality of said silicon film.

2. The film quality inspecting method according to claim 1, wherein the film quality of said silicon film is inspected by comparing a measurement result of the reflection intensity or reflectivity of the reflection beam to data stored beforehand.

3. The film quality inspecting method according to claim 1, wherein said measuring beam is applied to said silicon film at a plurality of positions thereon, and the reflection beams reflected from said plurality of positions by said silicon film are received to measure the intensity or reflectivity of each of said received beams and to set a threshold value, thereby inspecting the film quality of said silicon film at each of said plurality of positions based on said threshold thus set.

4. The film quality inspecting method according to claim 1, wherein said measuring beam is applied from a beam projecting section, and the reflection beam reflected by said silicon film is received by a beam receiving section.

5. The film quality inspecting method according to claim 4, wherein the measuring beam applied from said beam projecting section enters an optical filter so that a predetermined wavelength alone may pass therethrough.

6. The film quality inspecting method according to claim 4, wherein said beam projecting section and said beam receiving section are movably disposed to change an incident angle and a reflection angle of the measuring beam with respect to said perpendicular.

7. The film quality inspecting method according to claim 1, wherein a laser beam oscillated from a laser oscillator is applied to the silicon film on said substrate, whereby the silicon film is annealed.

8. The film quality inspecting method according to claim 7, wherein power of said laser oscillator is controlled on the basis of an inspection result of said film quality.

9. A film quality inspecting method comprising:
   applying a light beam to an annealed silicon film formed on a substrate;
   detecting a particle diameter of crystalline silicon of the silicon film in a first range size by receiving light having a first wavelength range reflected from the silicon film by the application;
   detecting a particle diameter of crystalline silicon of the silicon film in a second range size by receiving light having a second wavelength range reflected from the silicon film by the application; and
   inspecting a film quality of said silicon film based on determination results of the particle diameter of crystalline silicon of the silicon film in the first range size and the second range size.

10. The film quality inspecting method according to claim 9, wherein:
    said beam having said first range wavelength has at least one of wavelengths of 480 to 520 nm;
    said beam having said second range wavelength has at least one of wavelengths of 530 to 570 nm;
    said first detection signal is obtained by detecting a reflection beam, of said reflection beams, having a wavelength within a range of 480 to 520 nm; and
    said second detection signal is obtained by detecting a reflection beam, of said reflection beams, having a wavelength within a range of 530 to 570 nm.

11. The film quality inspecting method according to claim 9, wherein:
    the beams having said first range and second range wavelengths are scanned and applied to a predetermined region of said silicon film;
    said first and second detection signals are obtained by receiving the reflected beam sent from said predetermined region on said silicon film to thereby detect said reflection beams sent from a plurality of positions in said predetermined region; and
    said film quality is inspected on the basis of said first and second detection signals obtained corresponding to the same position of said plurality of positions.

12. The film quality inspecting method according to claim 9, wherein said first and second detection signals are obtained by selectively detecting reflection beams, of the beams reflected by said silicon film, having said first range and second range wavelengths.

13. A film quality inspecting apparatus comprising:
    a stage on which a substrate having a silicon film is mounted;
    optical devices which apply measuring beams having different wavelengths in specific ranges comprising a first range wavelength and a second range wavelength, emitted from a beam source on the silicon film of the substrate mounted on the stage approximately perpendicularly to the silicon film and which receive the reflected beams by means of an optical sensor; and a film quality measuring device which measures a particle diameter of crystalline silicon of said silicon film based on the reception by said optical sensor, said first range wavelength has at least one of wavelengths of 480 to 520 nm, and said second range wavelength has at least one of wavelengths of 530 to 570 nm.

14. The film quality inspecting apparatus according to claim 13, wherein said stage is movably disposed in a direction perpendicular to the measuring beam applied to said silicon film.

15. The film quality inspecting apparatus according to claim 13, wherein said beam source is a multi-color beam source.

16. The film quality inspecting apparatus according to claim 13, wherein each of said optical devices has a wavelength selection mechanism to select beams having wavelengths in specific ranges comprising the first range wavelength and the second range wavelength, a mirror to guide the beam selected by said wavelength selection mechanism to a predetermined direction, and an expansion optical system which expands the beam guided by said mirror to apply said beam to said silicon film.

17. The film quality inspecting apparatus according to claim 13, wherein said optical sensor is a two-dimensional sensor.

* * * * *